United States Patent [19]

Perälampi

[11] Patent Number: 5,541,184
[45] Date of Patent: * Jul. 30, 1996

[54] S-TIMOLOL HEMIHYDRATE TREATMENT PROCESS

[75] Inventor: Markku Perälampi, Kangasala, Finland

[73] Assignee: Leiras OY, Turku, Finland

[ * ] Notice: The term of this patent shall not extend beyond the expiration date of Pat. No. 5,231,095.

[21] Appl. No.: 320,327

[22] Filed: Oct. 11, 1994

Related U.S. Application Data

[62] Division of Ser. No. 910,789, Jul. 8, 1992, Pat. No. 5,354,860, which is a division of Ser. No. 663,853, filed as PCT/FI89/00196, Oct. 13, 1989 published as WO90/04592, May 3, 1990, Pat. No. 5,231,095.

[30] Foreign Application Priority Data

Oct. 20, 1988 [FI] Finland .................................. 884838

[51] Int. Cl.$^6$ ................................. A61K 31/535
[52] U.S. Cl. .......................................... 514/236.2
[58] Field of Search ............................ 514/236.2

[56] References Cited

U.S. PATENT DOCUMENTS 5,231,095 7/1993 Peralampi ............................ 514/236.2

FOREIGN PATENT DOCUMENTS 197504 10/1986 European Pat. Off. .

OTHER PUBLICATIONS

CAS Registry Handbook, Number Section, 1984, p. 2480 RM, Registry No. 91524–16–2.

"Nio–Pyrenol," Chemical Abstracts, Chemical Substance Index, vol. 106, p. 6752 CS, Jan.–Jun. 1987.

Chemical Abstract, vol. 106, No. 2, Jan. 12, 1987, p. 277 Abstract 93 70 k, Boudi et al.

Ullmann's Encyclopedia of Industrial Chemistry, Fifth, Completely Revised Edition. (1987); vol. A8, Wolfgang Gerhartz et al. "Coronary Therapeutics To Display Technology," pp. 6–7.

*Primary Examiner*—Philip I. Datlow

[57] ABSTRACT

A process for pharmaceutically treating a subject with S-(-)-3-morpholino-4-(3-tert-butylamino-2-hydroxypropoxy)-1,2,5-thiadiazole hemihydrate comprising preparing a composition containing the hemihydrate and topically applying the prepared composition to a surface of the subject.

9 Claims, 1 Drawing Sheet

S-TIMOLOL HEMIHYDRATE TREATMENT PROCESS

CROSS-REFERENCE TO RELATED APPLICATIONS

This application is a division of application Ser. No. 07/910,789 filed Jul. 8, 1992 now U.S. Pat. No. 5,354,860, which is a division of application Ser. No. 07/663,853 filed Apr. 19, 1991, (now issued as U.S. Pat. No. 5,231,095) which corresponds to PCT application Ser. No. PCT/FI89/00196 (WO 90/04592, May 3, 1990) filed Oct. 13, 1989 which corresponds to Finnish application Ser. No. 884838 filed Oct. 20, 1988. The priority of all of the foregoing applications is claimed hereby.

BACKGROUND OF THE INVENTION

The object of the present invention is a novel crystalline S-timolol derivative, in particular a novel hydrate form of S-timolol. The object of the invention is also a process for the preparation of this novel S-timolol derivative.

S-timolol, i.e., S-(-)-3-morpholino-4-(3-tert-butyl-amino-2-hydroxypropoxy)-1,2,5-thiadiazole and its acid addition salts, are known pharmacologically valuable β-blocking agents. In pharmaceutical preparations S-timolol is, as a rule, used as maleate salt, which, being a well crystallizing salt, has clear advantages compared to the free S-timolol base. The free S-timolol base is namely an oily sticky substance and thus difficult to process further, for example to purify and to dose. The use of the free S-timolol base in certain pharmaceutical preparations, especially in so called transdermal medicated patches or bandages, involves, however, advantages as compared to the acid addition salts as regards their penetration through the skin. Thus, the EP publication A2 0197504 discloses a transdermal delivery system, wherein use is made of i.a. timolol maleate, which is transformed to the nonionic, more easily absorbed timolol base form with a buffer. In the delivery system a solvent is used in which both the salt form and the free base form are soluble. The concentration of the timolol base form in the system is regulated with the pH of the buffer. From the viewpoint of easy manufacture of e.g. the transdermal system, it would be of advantage to prepare a S-timolol compound in the base form which crystallizes well in a non-sticky manner, which may be isolated in a pure form and which may be exactly dosed, and which at the same time exhibits a good penetration capacity when used in medicated bandages.

BRIEF SUMMARY OF THE INVENTION

Now it has surprisingly been discovered that S-timolol may easily be crystallized as the hemihydrate compound. Thus, the object of the invention is, as a novel compound, S-(-)-3-morpholino -4-(3-tert-butyl-amino-2-hydroxypropoxy)-1,2,5-thiadiazole hemihydrate of the formula

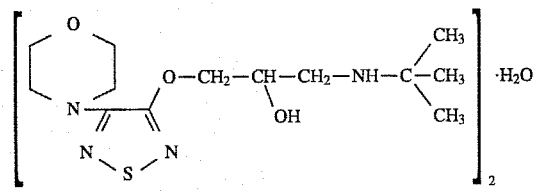

This compound, as obtained in a stable crystalline form, and the preparation thereof, are not known from the prior art.

The well-crystallized and stable compound according to the invention may thus find use in applications, e.g., medicated bandages, where the exact dosing of the active ingredient in base form is of importance.

The structure of the compound has been elucidated using X-ray diffraction. The results indicate for the compound a crystal structure wherein four S-timolol base molecules and two water molecules are situated in the same unit cell, the hydrophilic parts (—NH, —OH) of each pair of two S-timolol molecules being arranged around one water molecule. The hydrogen bridges formed by the water molecule and the two polar groups, along with the favourable lipophilic intermolecular forces, existing in the crystal lattice provide for optimal packing of the molecules. Because of the above-mentioned molecular arrangement, S-timolol hemihydrate may be crystallized in an optical purity of 100% e.e., which means that S-timolol hemihydrate and the crystallization procedure may also be used for purification purposes, e.g., small amounts of the corresponding R-timolol enantiomer generally encountered in the starting material prepared by any current method, may be removed completely. The molecular arrangement in the crystal lattice along with easily controlled crystal growth is the reason for this surprisingly simple removal of impurities in one single crystallization step.

BRIEF DESCRIPTION OF THE DRAWING

The appended FIG. 1 discloses the arrangement of S-timolol hemihydrate in the unit cell, omitting the hydrogen atoms.

DETAILED DESCRIPTION OF THE PREFERRED EMBODIMENT

Figure 1:
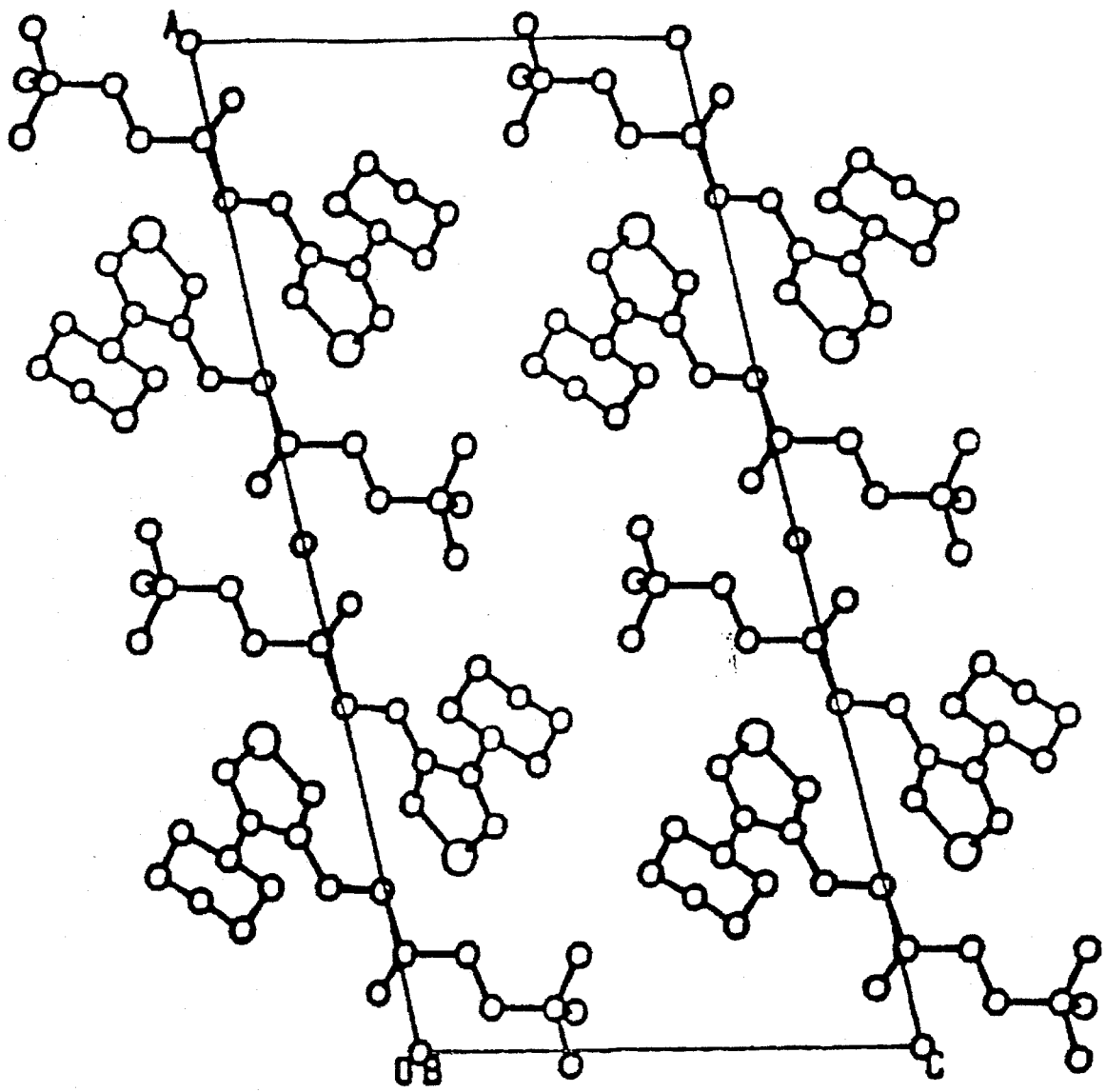

The crystal structure for S-timolol hemihydrate (single crystals from water-methylene chloride) was measured with a Enraf-Nonius CAD-4 diffractometer using graphite-monochromatized $MoK_\alpha$ (0.71073 Å) and ω-2θ method at 21° C. The cell parameters and orientation matrix were determined from 18 reflections (6°<θ<10°). The measuring rate (°min$^{-1}$) was 0.87–16.5, width (θ) 0.5+0.344 tan θ and area (θ) 2–25. The following crystal data were obtained: space group monoclinic, C2 (No. 5); a=23.435(3) Å, b=6.384(8) Å, c=11.591(1) Å, α=90.00°, β=103.081(1), γ=90.00, V=1687(3) Å, Z=2, d=1.281 gcm$^{-3}$.

The results obtained with a NMR spectrometer support the above obtained X-ray diffraction results (Instrument Bruker AC 250/Aspect 3000). $^1$H-NMR (solvent $CDCl_3$) δ (ppm): 1.09 (s, 9H), 2.0 (b, appr. 2.5H), 2.57 (d+d, 1H; 12.0 and 8.0 Hz), 2.80 (d+d, 1H; 12.0 and 4.0 Hz), 3.52 (m, 4H), 3.79 (m, 4H), 3.91 (m, 1H), 4.36 (d+d, 1H; 11.1 and 5.8 Hz), 4.47 (d+d, 1H; 11.1 and 4.1Hz).

$^{13}$C-NMR (solvent $CDCl_3$) δ (ppm): 28.91 (q), 50.24 (s), 44.33 (t), 66.10 (d), 72.76 (t), 153.66 (S), 149.78 (s), 47.78 (t), 66.33 (t).

S-timol hemihydrate has also been analyzed thermogravimetrically (Perkin Elmer, TGS-2 thermogravimetric analyzer and attached differential scanning DSC 4 calorimeter). The TG graph indicates splitting off of the hydrate water at about 50° C., the DSC gives a melting point of 53.3° C.

According to the invention the novel crystalline S-timolol hemihydrate may be prepared in a very simple manner by crystallizing the same from a solution prepared with an aqueous organic solvent or solvent mixture of the S-timolol base. As a starting material, also a salt of the S-timolol base, for example the maleate salt, may be used, whereby the free S-timolol base is first liberated with an alkaline agent, especially with sodium hydroxide, and the hemihydrate is thereafter crystallized as described above. As already mentioned earlier, the starting material may contain small amounts of impurities, e.g. in form of the corresponding R-timolol base or the corresponding salt, respectively, which R-enantiomer may be removed completely in a single crystallization step, to give the desired S-timolol hemihydrate in optically pure form. When the process is used for purification purposes, the pure hemihydrate thus obtained may then be converted back to the free S-timolol base or its salt.

In the process, any organic solvent or solvent mixture may be used in which the S-timolol base dissolves but in which, in the presence of water, the formed hemihydrate is sparingly soluble. The process is generally carried out by forming a solution of the S-timolol base with an organic solvent. Water is added in an amount sufficent for the formation of the hemihydrate, and the S-timolol hemihydrate is allowed to crystallize. As the organic solvent which dissolves the timolol base, for example, an aromatic hydrocarbon, such as toluene or xylene, especially toluene, an ether-type solvent, such as di-isopropyl ether, an alcohol, such as ethanol, or a chlorinated hydrocarbon, such as methylene chloride, may be used. The solubilities of the timolol base and the hemihydrate may be regulated by means of an additional organic solvent, or in some cases by the amount or ratio of water used. Thus, for example, an aliphatic hydrocarbon, such as hexane, may be used as a solvent component which reduces the solubility of the hemihydrate. In the system, the amount of water may vary from the stochiometric amount to an amount greatly exceeding the stochiometric amount, e.g. up to 20–30 times the stochiometric amount. Rather than crystallizing the hemihydrate from the aqueous solvent mixture, proper crystallization is also achieved by evaporating the organic solvent component, preferably a low-boiling one, while retaining a sufficient amount or ratio of water. The solvent may if needed, be heated to facilitate dissolution of the timolol base, and after the addition of water and possibly auxiliary solvent, the mixture is preferably stirred to facilitate the formation and crystallization of the hemihydrate. As regards the volume ratio between water and organic solvent, generally organic solvent is used in an excess. From a process technical viewpoint, a suitable ratio could be, e.g., from about 1:5 to 1:30.

The identity of crystals obtained from the different above mentioned procedures was confirmed by comparing their powder X-ray diffraction patterns.

Pharmaceutical dosage forms may be prepared from the S-timolol hemihydrate for enteral or parenteral and especially for topical administration, e.g., tablets, capsules, solutions, suspensions and emulsions, and especially transdermal administration forms for transdermal administration. Conventional organic or inorganic adjuvants may be used in the pharmaceutical preparations in a manner known to the man skilled in the art.

The following examples illustrate the invention without limiting its scope.

EXAMPLE 1

S-(-)-3-morpholino-4-(3-tert-butylamino-
2-hydroxypropoxy)-1,2,5-thiadiazole hemihydrate
(S-timolol hemihydrate 366 g of S-timolol base are dissolved in 1.5 liters of toluene. The solution is cooled to 0° C. 175 ml of water and thereafter 875 ml of hexane are added while vigorously stirring. Crystallization sets in after approximately 30 to 60 minutes.

Thereafter stirring is continued for about 30 minutes. 25 ml of water and 1750 ml of hexane are added, whereafter mixing is continued for about 2 hours at 0° C. The precipitate is filtered and washed with appr. 300 ml of hexane. Drying is carried out at room temperature.

335 g (89%) of the title product are obtained, m.p. 48° to 50° C. (capillary tube). Optical purity 100% e.e., $[\alpha]25°/405=-16.0°$.

EXAMPLE 2

S-(−)-3-morpholino-4-(3-tert-butylamino-
2-hydroxypropoxy)-1,2,5-thiadiazole hemihydrate
(S-timolol hemihydrate 500 g of S-timolol maleate are weighed into a flask and 2 liters of water are added. Stirring is continued for about 10 minutes, 1 liter of toluene is added and the mixtured is cooled to about 15° C., at which temperature a 47% NaOH solution is added dropwise until the pH is about 12.5. The phases are separated. The toluene phase is recovered and the water phase is re-extracted with 0.5 liters of toluene. The toluene phases are combined and washed with water. The toluene solution is cooled to 0° C. 175 ml of water are added and thereafter 875 ml of hexane while vigorously stirring. Crystallization sets in after about 30 to 60 minutes. Thereafter stirring is continued for about 30 minutes. 25 ml of water and 1750 ml of hexane are added, whereafter stirring is continued for about 2 hours at 0° C. The precipitate is filtered and washed with about 300 ml of hexane. Drying is effected at room temperature.

335 g of the title compound are obtained (89% calculated on the S-timolol maleate), m.p. 48° to 50° C. (capillary tube). Optical purity 100% e.e., $[\alpha]25°/405=-16.0°$.

EXAMPLE 3

S-(-)-3-morpholino-4-(3-tert-butylamino-
2-hydroxypropoxy)-1,2,5-thiadiazole hemihydrate
(S-timolol hemihydrate 100 g of S-timolol base are dissolved in 500 ml of diisopropyl ether while boiling. 50 ml of water are added and the mixture is cooled to +10° to +20° C. 0.1 g of S-timolol hemihydrate is added as a seed while vigorously stirring. After the crystallization has set in the mixture is cooled to 0° C., at which temperature stirring is continued for 1 hour. The crystals are filtered, washed with diisopropyl ether and dried below 4° C. The yield is 81 g (79%) of S-timolol hemihydrate, m.p. 48° to 50° C. (capillary tube). Optical purity 100% e.e., $[\alpha]25°/405=-16.0°$.

I claim:

1. Process for pharmaceutically treating a subject with S-(-)-3-morpholino-4-(3-tert-butyl-amino-2-hydroxypropoxy)-1,2,5-thiadiazole hemihydrate comprising the steps of:

preparing a composition containing S-(-)-3-morpholino-4-(3-tert-butyl-amino-2-hydroxypropoxy)-1,2,5-thiadiazole hemihydrate; and topically applying the prepared composition to a surface of the subject.

2. The process of claim 1 wherein the step of preparing comprises synthesizing S-(-)-3-morpholino-4-(3-tert-butyl-amino-2 -hydroxypropoxy)-1,2,5-thiadiazole hemihydrate.

3. The process of claim 2 wherein the step of preparing further comprises admixing selected pharmaceutically acceptable adjuvants together with the synthesized S-(-)-3-morpholino-4-(3-tert-butyl-amino-2-hydroxypropoxy)-1,2,5-thiadiazole hemihydrate.

4. The process of claim 1 wherein the step of preparing comprises forming the composition into an aqueous solution.

5. The process of claim 4 wherein the composition is formed into a dosage form.

6. The process of claim 2 wherein the step of preparing further comprises forming the composition into an aqueous solution.

7. The process of claim 6 wherein the composition is formed into a dosage form.

8. The process of claim 3 wherein the step of preparing further comprises forming the composition into an aqueous solution.

9. The process of claim 8 wherein the composition is formed into a dosage form.

* * * * *